United States Patent [19]

Henderson, Jr.

[11] Patent Number: 4,568,761

[45] Date of Patent: Feb. 4, 1986

[54] PROCESS FOR PREPARING TERTIARY ARALKYL CARBAMATES FROM TERTIARY ARALKYL CHLORIDES

[75] Inventor: William A. Henderson, Jr., Stamford, Conn.

[73] Assignee: American Cyanamid Company, Stamford, Conn.

[21] Appl. No.: 643,119

[22] Filed: Aug. 22, 1984

[51] Int. Cl.$^4$ .............. C07C 125/065; C07C 125/073
[52] U.S. Cl. ..................................... 560/024; 560/25; 560/30
[58] Field of Search .......................... 560/24, 25, 30

[56] References Cited

FOREIGN PATENT DOCUMENTS 0021012  1/1981  European Pat. Off. ............. 560/24

Primary Examiner—Bernard Helfin
Attorney, Agent, or Firm—Gordon L. Hart

[57] ABSTRACT

A new and improved process for preparing tertiary aralkyl carbamates is disclosed. The process comprises reacting a mixture of a lower alkyl carbamate with a tertiary aralkyl halide at a temperature of about 50° C. to about 100° C. until formation of the tertiary aralkyl carbamate is substantially complete. In a preferred process, an alkenyl aromatic compound which is the olefin precursor of the aralkyl halide employed, is added to the reaction mixture to improve the yield of tertiary aralkyl carbamate products. The tertiary aralkyl carbamates prepared by the process of this invention are useful intermediates which may be thermally cracked in the presence of base catalysts to form tertiary aralkyl isoayanates.

7 Claims, No Drawings

PROCESS FOR PREPARING TERTIARY ARALKYL CARBAMATES FROM TERTIARY ARALKYL CHLORIDES

The present invention relates to the preparation of tertiary aralkyl biscarbamates and carbamates which may be employed in thermal cracking processes to produce useful aralkyl isocyanate compounds. More particularly, it relates to a process for making tertiary aralkyl carbamates by reacting a lower alkyl urethane compound and a tertiary aralkyl halide compound.

The use of tertiary aralkyl carbamate compounds as starting materials for the production of useful tertiary aralkyl isocyanate compounds is presently known. In U.S. patent application Ser. No. 400,799, filed July 22, 1982 and now U.S. Pat. No. 4,439,616, for example, there is disclosed a method for production of tertiary aralkyl isocyanate compounds, such as tetramethylxylylenediisocyanate (TMXDI), by the thermal cracking of corresponding tertiary aralkyl biscarbamates, e.g., tertiary aralkyl diurethanes. As is disclosed therein, the tertiary aralkyl carbamate compounds may be produced by an addition reaction of lower alkyl esters of carbamic acid to corresponding alkenyl aromatic compounds at moderate temperatures in the presence of an acid catalyst. The thermal cracking of these tertiary aralkyl carbamate compounds is a particularly useful method for preparing meta- and para-isomers of TMXDI and, as a byproduct thereof, substantial amounts of the corresponding meta- or para-isopropenyl-α,α-dimethyltolyisocyanate (m-TMI and p-TMI, respectively) are formed. The m-TMI or p-TMI compounds produced may be recycled in the process to improve the overall yield of TMXDI obtained. However, the TMI compounds have substantial utility per se as distinct products and are homopolymerizable and copolymerizable by virtue of their ethylenic unsaturation to form useful polymers containing crosslinkable isocyanate functionality.

It has now been discovered that useful tertiary aralkyl carbamate intermediates may be prepared directly from tertiary aralkyl halides and lower alkyl carbamates upon heating to a temperature of between about 50° C. to about 100° C., without the need for a catalyst. It has further been discovered that additional amounts of tertiary aralkyl carbamates may be obtained if, in addition to the tertiary aralkyl halide compound, an alkenyl aromatic compound, typically, the diolefin precursor of the aralkyl halide, is added to the reaction mixture.

In accordance with the present invention, a new and improved process for preparing tertiary aralkyl carbamates is provided. The process of this invention comprises:

(a) providing a reaction mixture comprising:
 (i) a tertiary aralkyl halide compound of the general formula:

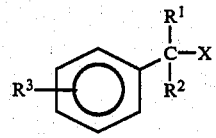

wherein $R^1$ and $R^2$ are each independently selected from $C_1$ to $C_{12}$ alkyl; X is halogen and $R^3$ is hydrogen, halogen, alkyl, haloalkyl, alkenyl, phenyl, alkyl-, alkenyl- or haloalkyl-substituted phenyl; and (ii) a lower alkyl carbamate compound of the general formula

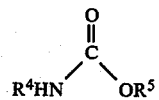

wherein $R^4$ is hydrogen or lower alkyl and $R^5$ is $C_1$ to $C_{12}$ alkyl; and (b) heating said reaction mixture at a temperature of between about 50° C. to about 100° C. until formation of the tertiary aralkyl carbamate compound is substantially complete.

In a preferred embodiment the tertiary aralkyl halide comprises m- or p-tetramethylxylylene dichloride and the lower alkyl carbamate comprises methyl carbamate to yield a reaction product comprising m- or p-tetramethylxylylene bis(methyl carbamate) (m- or p-TMXDU). Generally, and without limitation, the reaction mixture is heated at between about 50° C. to about 100° C. for about from 4 to 25 hours to produce the tertiary aralkyl carbamate in good yield.

It has also been discovered that additional amounts of the tertiary aralkyl carbamates may be obtained in accordance with the method of the present invention by the addition of an alkenyl aromatic compound which is an olefin precursor of the tertiary aralkyl halide starting material employed.

Generally, the reaction between the lower alkyl carbamates and the tertiary aralkyl halides will proceed using a broad range of proportions of starting materials. Typically, the molar ratio of the lower alkyl carbamate to the tertiary aralkyl halide employed, without limitation, will be in the range of from about 1:1 to about 20:1, respectively, and preferably a range of from about 5:1 to about 10:1 is employed.

It has also been discovered that if an alkenyl aromatic compound, generally the corresponding olefin precursor to the tertiary aralkyl halide, is added to the reaction mixture, the relative proportion of the tertiary aralkyl halide compound employed may be substantially reduced and good yields of the tertiary aralkyl carbamates still be obtained. In this preferred embodiment of the present invention, the relative proportions of lower alkyl carbamate to alkenyl aromatic compound to tertiary aralkyl halide may, without limitation, range from about 2:1:1 to about 20:10:1, respectively.

Other objects and advantages of the present invention will become apparent from the following detailed description taken in conjunction with the illustrative working Examples.

In accordance with the present invention, a new and improved process for the preparation of useful tertiary aralkyl carbamates comprises reacting a lower alkyl carbamate compound with a tertiary aralkyl halide compound at a temperature of from about 50° to about 100° C. for a time sufficient to allow the reaction to proceed substantially to completion.

More particularly, the lower alkyl carbamates for use in the process of the present invention are compounds represented by the general formula:

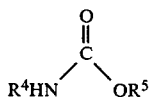

wherein $R^4$ is hydrogen or $C_1-C_{12}$ alkyl and $R^5$ is $C_1-C_{12}$ alkyl. Illustrative examples of suitable lower alkyl carbamates for use herein are: methylcarbamate, ethylcarbamate, propylcarbamate, butylcarbamate, N-methyl-methylcarbamate, N-methyl-ethylcarbamate, N-ethyl-ethylcarbamate, N-butyl-methylcarbamate, and the like, to name but a few. The preferred lower alkyl carbamate for use herein is methylcarbamate.

The lower alkyl carbamate compounds for use herein are extremely well known and abundantly commercially available compounds. They may be prepared, however, by several known methods, such as, for example, by reacting primary isocyanate compounds or urea with lower, e.g. $C_1-C_{12}$, alkanols.

The tertiary aralkyl halide compounds for use in the process of the present invention comprise compounds having the general formula:

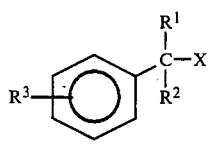

wherein $R^1$ and $R^2$ are each independently selected from $C_1$ to $C_{12}$ alkyl; X is halogen and $R^3$ is hydrogen, alkyl, haloalkyl, alkenyl, phenyl, alkyl-substituted phenyl, alkenyl-substituted phenyl or haloalkyl-substituted phenyl.

Illustrative of suitable tertiary aralkyl halide compounds for use herein are, for example, α,α-dimethylbenzylchloride, α,α-dimethylbenzylbromide, α,α-dimethylbenzyliodide, α-methyl-α'-ethylbenzyl chloride, α-chloro-α,α-diemthyl-m- or p-xylene, m- or p-chloroethyl-α,α-dimethyltolylchloride, m- or p-isopropenyl-α,α-dimethyltolylchloride, m- or p-tetramethylxylylenedichloride, m- or p-tetramethylxylylenedibromide, and the like. The preferred tertiary aralkyl halides for use as starting materials herein are m- or p-isopropenyl-α,α-dimethyltolylchloride and m- or p-tetramethylxylylenedichloride.

The tertiary aralkyl halides may be simply prepared by the addition of a hydrogen halide to a corresponding alkenyl aromatic compound. By way of illustration, for example, dry halogen chloride gas may be passed directly into m- or p-diisopropenylbenzene to yield m- or p-tetramethylxylylene-dichloride. The preparation of the tertiary aralkyl halides by addition of hydrogen halides to alkenyl aromatic compounds is extremely well known to those skilled in this art.

In accordance with a preferred embodiment of this invention, an alkenyl aromatic compound will be added to the reaction mixture comprising the lower alkyl carbamate and the tertiary aralkyl halide to improve the overall amount of tertiary aralkyl carbamate obtained.

The alkenyl aromatic compounds for use in this embodiment of the present invention will generally comprise the olefin or diolefin precursors of the tertiary aralkyl halide employed. The alkenyl aromatic compounds for use herein generally comprise compounds of the formula:

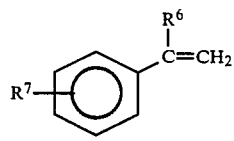

wherein $R^6$ is hydrogen or lower alkyl and $R^7$ is hydrogen, halogen, alkyl, substituted alkyl, alkenyl, phenyl or substituted phenyl.

In order to improve the yield of the desired tertiary aralkyl carbamate to be prepared, the alkenyl aromatic compound should be the olefin precursor of the tertiary aralkyl halide employed. Thus, for example, if the aralkyl halide used is α,α-dimethylbenzyl chloride, the corresponding alkenyl aromatic compound to be added is α-methylstyrene, and if the aralkyl halide is m- or p-tetramethylxylylenedichloride, the alkenyl aromatic compound to be added is the corresponding m- or p-diisopropenylbenzene.

The alkenyl aromatic compounds for use herein are also extremely well known and are abundantly available commercially. They may be prepared by Friedel-Crafts alkylation of benzene with the alkyl halide and aluminum chloride followed by dehydrogenation to form the alkenyl aromatic products, to name but one method.

The reaction in accordance with the process of the present invention may generally be summarized, in terms of preferred starting materials, as follows:

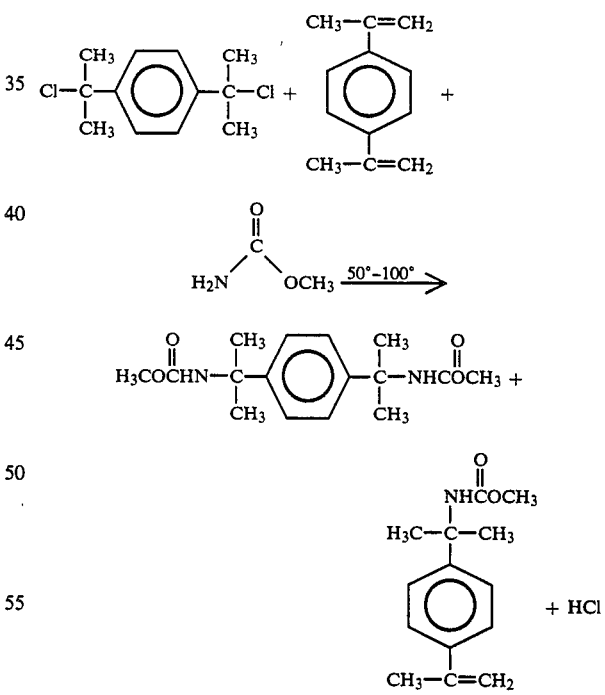

The reaction proceeds upon heating the reaction mixture at temperatures of between about 50° C. to about 100° C. and generally formation of the tertiary aralkyl carbamates is substantially complete in from about 1 to 25 hours. Preferably, the reaction mixture will be heated for from about 6 to about 20 hours.

The reaction will proceed using broad ranges of the components. Generally an excess of the lower alkyl carbamate will be used, although the reaction will proceed with approximately stoichiometric amounts of the starting materials. Good results have been obtained using molar ratios of the lower alkyl carbamate compound to the tertiary aralkyl carbamate of from about 1:1 to about 20:1, respectively. In the preferred process, wherein the corresponding alkenyl aromatic compound is added to the reaction mixture along with the other starting materials, good results may be obtained using molar ratios of lower alkyl carbamate to alkenyl aromatic compound to tertiary aralkyl halide of from about 2:1:1 to about 20:10:1, respectively.

The reaction may be carried out with or without an organic solvent. If it is desired to use a solvent, any non-polar organic solvent may be employed for example, alkyl halides such as methylene chloride or dichloroethane and aromatic solvents such as benzene, toluene, xylene, and the like. The preferred solvent, if used, is dichloroethane.

In order that those skilled in the art may better understand how the present invention may be practiced, the following examples are provided by way of illustration and not by way of limitation.

EXAMPLE 1

SYNTHESIS OF p-TETRAMETHYLXYLENE BIS(METHYLCARBAMATE) (P-TMXDU)

A solution was prepared by admixing 10 mmoles of p-tetramethylxylylenedichloride and 80 mmoles of methyl carbamate in 10 mls of 1,2-dichloroethane in a reaction vessel equipped with a stirrer. The reaction mixture was heated with stirring at 60° C. for 16 hours. Thereafter the product mixture was analyzed by gas chromatography and was found to contain 1.0 mmole of the starting dichloride, 4.0 mmoles of the intermediate monochloromonocarbamate, i.e. p-2-chloroisopropyl-α,α-dimethyltolylchloride, and 2.8 mmoles of p-tetramethylxylenebis(methyl carbamate).

EXAMPLE 2

This example demonstrates the improved yields obtained by adding a diolefin precursor to the reaction mixture.

A reaction mixture was prepared by admixing 9 mmoles of m-diisopropylbenzene, 1 mmole of m-tetramethylxylylenedichloride, and 10 mmoles of methyl carbamate in 10 mls of 1,2-dichloroethane, in a reaction vessel equipped with a stirrer. The reaction mixture was heated with stirring at 60° C. for 16 hours. The product mixture was analyzed by gas chromatography in accordance with the method of Example 1 and was found to contain 0.1 mmoles of the diolefin, 1.6 mmoles of the monochloromonocarbamate and 7.8 mmoles of m-tetramethylxylylenebis(methyl carbamate).

The biscarbamate product was thereafter recrystallized from ethyl acetate. The purified m-tetramethylxylylenebis(methyl carbamate) had a melting point of 129° C.–131° C. and had an IR spectrum identical to that of m-tetramethylxylylenebis(methyl carbamate) prepared by a different method.

EXAMPLE 3

In accordance with the procedures of Example 1, a mixture of 9.5 mmoles of p-diisopropenylbenzene, 0.5 mmole of p-tetramethylxylylenedichloride and 10 mmoles of methyl carbamate in 10 ml of 1,2-dichloroethane was heated at 60° C. for 14 hours. Analysis of the product mixture by gas chromatography showed the presence of p-isopropenyl-alpha,alpha-dimethyltolyl(methyl carbamate) plus lesser amounts of the diolefin and p-tetramethylxylylenebis(methylcarbamate).

EXAMPLE 4

SYNTHESIS OF α,α-DIMETHYLTOLYL(METHYL CARBAMATE)

In accordance with the procedures of Example 1, an aralkylmonocarbamate compound was prepared as follows:

A mixture of 1 mmole of α,α-dimethylbenzylchloride, 9 mmoles of α-methylstyrene and 60 mmoles of methyl carbamate was heated with stirring at 60° C. for 6 hours.

Analysis of the product mixture by gas chromatography showed 8.5 mmoles of α,α-dimethylbenzyl (methyl carbamate).

The new and improved process of the present invention provides useful tertiary aralkyl carbamate compounds, suitable for use as starting materials in a base catalyzed thermal cracking process, such as the process described in U.S. Ser. No. 400,799, filed July 22, 1982 and now U.S. Pat. No. 4,439,616.

All of the above mentioned patents and applications are specifically incorporated herein by reference.

Although the present invention has been described with reference to certain preferred embodiments it is apparent that modifications or changes may be made therein by those skilled in this art. For example, instead of tertiary aralkyl chlorides, tertiary aralkyl bromides and tertiary aralkyl iodides may be used. All such obvious modifications or changes may be made herein without departing ftom the scope and spirit of the present invention, as defined by the appended claims.

I claim:

1. A process for the preparation of tertiary aralkyl carbamates, said process comprising:
   (a) providing a reaction mixture comprising a tertiary alkyl halide having the formula:

$$R^3 - \underset{}{\bigcirc} - \underset{R^2}{\overset{R^1}{\underset{|}{C}}} - X$$

wherein $R^1$ and $R^2$ are each, independently, selected from $C_1$ to $C_{12}$ alkyl, X is halogen and $R^3$ is hydrogen, alkyl, haloalkyl, alkenyl, phenyl or alkyl-, alkenyl- or haloalkyl-substituted phenyl and a lower alkyl carbamate having the formula:

$$\underset{R^4HN}{\overset{O}{\underset{}{\overset{\|}{C}}}}\diagdown_{OR^5}$$

wherein $R^4$ is hydrogen or lower alkyl and $R^5$ is $C_1$ to $C_{12}$ alkyl, the molar ratio of said carbamate to said halide in said reaction mixture being from about 1:1 to about 20:1; and (b) heating said reaction mixture at a temperature of between 50° C. to about 100° C. until formation of the tertiary aralkyl carbamate compound is substantially complete.

2. A process as recited in claim 1, wherein said tertiary aralkyl halide compound is m-tetramethylxylylene dichloride.

3. A process as recited in claim 1 wherein said tertiary aralkyl halide compound is p-isopropenyl-α,α-dimethyltolyl dichloride.

4. A process as recited in claim 1, wherein said lower alkyl carbamate compound is methyl carbamate.

5. A process as recited in claim 1, wherein the reaction mixture of step (a) further comprises an alkenyl aromatic compound of the formula:

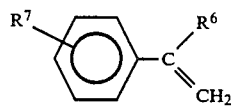

wherein $R_6$ is hydrogen or lower alkyl and $R^7$ is hydrogen, halogen, alkyl, substituted alkyl, alkenyl, phenyl and substituted phenyl the molar ratio of carbamate to alkenyl aromatic compound to halide in said reaction mixture being in the range from about 2:1:1 to about 20:10:1.

6. A process as recited in claim 1, wherein the reaction mixture of step (a) additionally comprises m- or p-diisopropenylbenzene.

7. A process as recited in claim 1, wherein said reaction mixture is heated for a period of from about 4 to about 25 hours.

* * * * *